United States Patent [19]

Bricker et al.

[11] Patent Number: 5,422,393

[45] Date of Patent: * Jun. 6, 1995

[54] NATRIURETIC HORMONE

[75] Inventors: Neal S. Bricker; William J. Wechter, both of Redlands, Calif.

[73] Assignee: Naturon Pharmaceutical Corporation, New Canaan, Conn.

[ * ] Notice: The portion of the term of this patent subsequent to Apr. 21, 2009 has been disclaimed.

[21] Appl. No.: 135,364

[22] Filed: Oct. 12, 1993

Related U.S. Application Data

[60] Continuation of Ser. No. 993,501, Dec. 17, 1992, abandoned, which is a continuation of Ser. No. 776,497, Oct. 11, 1991, abandoned, which is a division of Ser. No. 537,869, Jun. 13, 1990, Pat. No. 5,106,630, which is a continuation of Ser. No. 426,497, Oct. 23, 1989, abandoned, which is a continuation of Ser. No. 217,458, Jul. 11, 1988, abandoned.

[51] Int. Cl.$^6$ .............................................. A61K 35/04
[52] U.S. Cl. ..................................... 424/520; 424/528; 424/529; 424/543; 424/545; 514/169; 514/869; 514/65; 514/505; 552/502
[58] Field of Search ............... 424/520, 528, 529, 543, 424/545; 514/65, 869, 169, 505; 552/502

[56] References Cited

U.S. PATENT DOCUMENTS 4,780,314 10/1988 Graves ................................. 424/520
5,106,630 4/1992 Bricker et al. ...................... 424/520

*Primary Examiner*—Marianne M. Cintins
*Assistant Examiner*—T. J. Criares
*Attorney, Agent, or Firm*—Weingarten, Schurgin, Gagnebin & Hayes

[57] ABSTRACT

A purified naturally occurring natriuretic compound, identified as Natriuretic Hormone, and a method for isolation of the compound. The natriuretic compound has a molecular weight of about 360, a molecular formula of $C_{21}H_{28}O_5$ and with a steroidal nucleus. The compound is useful as a diuretic in the treatment of diseases such as heart disease and hypertension.

16 Claims, 1 Drawing Sheet

NATRIURETIC HORMONE

RELATED APPLICATION

This application is a continuation application of prior application Ser. No. 07/993,501, filed on Dec. 17, 1992, now abandoned which in turn is a continuation of Ser. No. 07/776,497, filed on Oct. 11, 1991, now abandoned which in turn is a division application of Ser. No. 07/537,869, filed on Jun. 13, 1990, now U.S. Pat. No. 5,106,630 which is a continuation of 07/426,497, filed on Oct. 23, 1989, now abandoned which in turn is a continuation of Ser. No. 07/217,458, filed on Jul. 11, 1988, now abandoned.

FIELD OF THE INVENTION

This invention relates to a compound having a natriuretic effect which can be used to increase sodium excretion in man or other mammals.

BACKGROUND OF THE INVENTION

The nature of the system controlling sodium excretion in man and other terrestrial mammals has been investigated for many years. Until the early 1960's, sodium excretion in mammals was believed to be controlled by changes in one of two factors: 1) glomerular filtration rate ("GFR"); and 2) mineralocorticoid hormone activity. In 1961, however, it was demonstrated by DeWardener et al., *Clinical Science*, Vol. 21, pp. 249-258 (1961), that an additional factor, or factors, regulated sodium excretion. It was observed that increased sodium excretion (hereinafter referred to as "natriuresis") occurred in response to extracellular fluid volume expansion in dogs despite constant GFR and mineralocorticoid hormone activity.

Since the observations of DeWardener et al., considerable effort has been employed by researchers in the field to isolate and identify other factors involved in the regulation of sodium excretion. In the belief that there exists a principal modulator of sodium excretion, a number of researchers have pursued a substance referred to as the "natriuretic hormone." See, e.g., Bricker, N. S., "The Control of Sodium Excretion With Normal and Reduced Nephron Populations: Pre-Eminence of Third Factor,"*Am. J. Med.*, 43:313 (1967); see also Haber and Haupert, Hypertension, 4:315 (1987).

Prior to the present invention, natriuretic factors acting on the Na/K/ATPase pump had not been isolated in pure form, chemically defined, or synthesized in the laboratory. In fact, there is evidence that more than one biochemical compound may be responsible for observed effects. The inhibitors of active sodium transport inhibiting fractions studied by most investigators is a small molecule with a molecular weight of less than 500 Daltons (as indicated by ultra filtration). Some groups have reported that the compound could be a peptide, but recent studies have not supported the peptide nature of the factor.

Considerable research over the last several decades has focused on adverse effects of a high sodium diet (for example in hypertension) and on the renal retention of sodium in a number of diseases, including heart disease, liver failure and pre-menstrual syndromes. Diuretic agents are widely used today in an effort to prevent or reverse these pathologic states. However, most potent widely used diuretics not only increase sodium excretion but may also lead to undesirable loss of potassium. Unfortunately, the potassium supplements prescribed for replacement are generally unpalatable, expensive and difficult for patients to tolerate on a continuing basis.

There thus exists a need for a potent natriuretic compound which specifically augments sodium excretion but does not produce the loss of potassium. The present invention satisfies this need and provides related advantages as well.

SUMMARY OF THE INVENTION

The present invention provides a substantially purified natriuretic compound, termed "Natriuretic Hormone" that increases sodium excretion without adversely affecting potassium excretion. The Natriuretic Hormone has a steroidal nucleus, a molecular weight of 360.4 and a molecular formula of $C_{21}H_{28}O_5$.

In one aspect of the invention, the Natriuretic Hormone is obtained by lyophilizing and reconstituting at a reduced volume with deionized water the urine from uremic patients to obtain concentrated samples, separating the concentrated material by gel filtration, subjecting the post salt peak to reverse-phase high pressure liquid chromatography using a pyridinium acetate/methanol buffer. The biologically active material activity is eluted with about 45% methanol. The purified product of the HPLC is then trimethylsilylated and subjected to gas chromatography at elevated temperature. The single product of this chromatography is then hydrolyzed in acid solutions to yield after evaporation the Natriuretic Hormone.

In another aspect of the invention, the Natriuretic Hormone is used to increase the sodium excretion in a mammal.

DETAILED DESCRIPTION OF THE INVENTION

Figure 1:
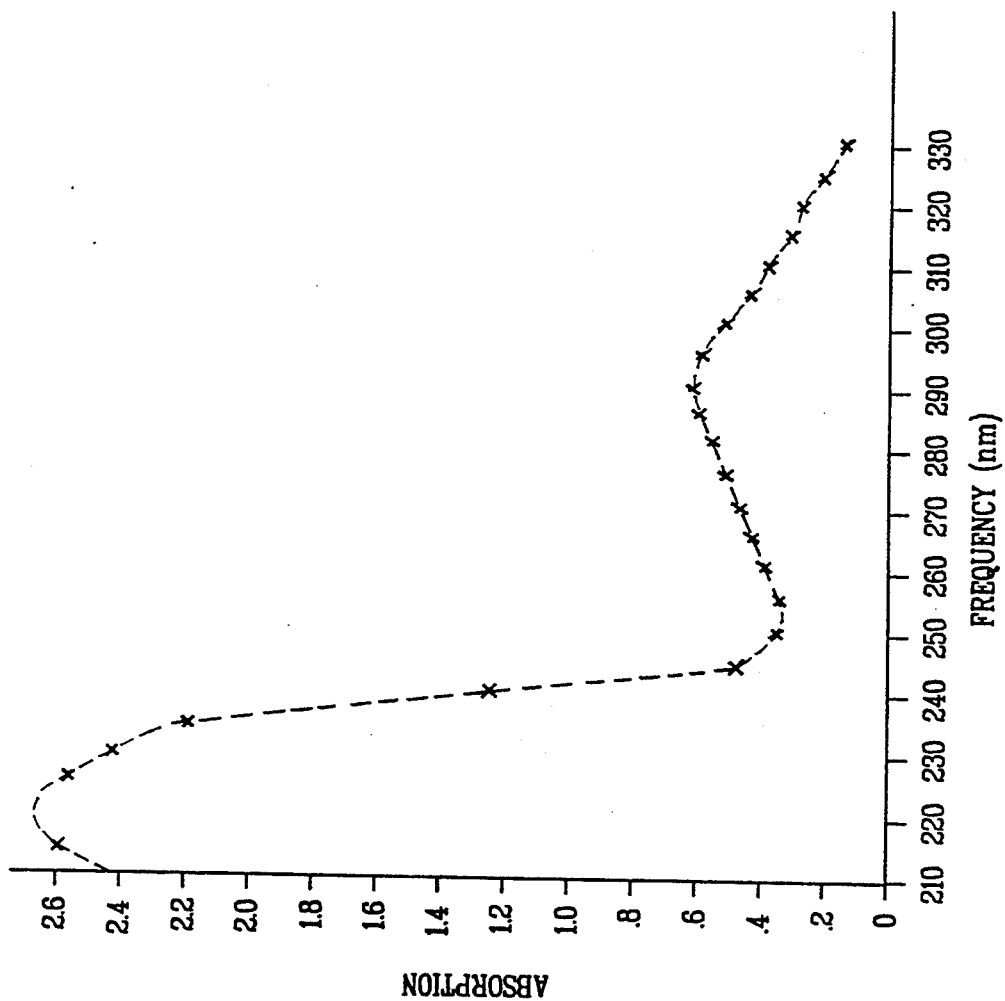
FIG. 1 provides a representation of an ultra violet absorption spectra of a purified active sample as described in Example I.

In the course of investigations leading to the present invention, a compound having natriuretic properties was isolated, in substantially pure form. The compound is termed the Natriuretic Hormone. This Natriuretic Hormone can be obtained from a variety of sources, including the blood and urine of mammals, preferably humans or dogs and homogenates of selected tissues such as the hypothalamus. Although the compound is present in normal human urine, the amount harvested per 24 hour urine collection is markedly greater in urine from uremic individuals.

The Natriuretic Hormone has molecular weight of 360.4, a molecular formula of $C_{21}H_{28}O_5$ and a steroidal nucleus. Additional information relating to the physical properties of the Natriuretic Hormone is also available. It has been isolated as a white powder and exhibits a major ultraviolet absorbance peak at about 220 nm and a broad secondary peak at about 290 nm. The Natriuretic Hormone has been found to be highly resistant to temperature extremes, maintaining biologic activity as described below after over a year of exposure to minus 80° C. or vigorous boiling. It is water soluble and has also been found to be soluble in certain organic solvents with high dielectric constants, indicating its polar nature. It is eluted from a Sephadex G-25 column employing ammonium acetate (NH4O Ac) buffer, pH 6.8, and appears after the salt peak.

The biological activity of the Natriuretic Hormone is markedly decreased by exposure to 5N HCl. It appears that the reaction taking place is due to interaction of acid with hydroxyl, carbonyl, or carboxy groups on the steroidal nucleus, which are known to undergo elimination (e.g., dehydration), rearrangement (e.g., reverse aldol), and/or hydrolysis (e.g., lactone cleavage) reactions in appropriate circumstances.

Additionally, the Natriuretic Hormone can be further purified using a high pressure liquid chromatography (HPLC) column (reverse-phase HPLC using a C-18 resin column) employing a 0.2 m pyridinium acetate buffer (PH 5.5)/methanol gradient, followed by repeated isocratic elution from the same column at a methanol concentration of about 40 to 50%, preferably 45%.

As used herein, the term "Natriuretic Hormone" refers to a compound which increases the rate of sodium excretion in at least one mammal upon administration by inhibiting Na-K-ATPase activity in the nephron. The native human Natriuretic Hormone has a molecular weight of 360.4, a molecular formula of $C_{21}H_{28}O_5$ and asteroid nucleus.

The term Natriuretic Hormone refers to both the native hormone and in vitro or in vivo modifications which retain natriuretic activity. It is understood that limited modifications, substitutions or deletions of functional groups may be made without destroying the biological activity. Moreover, it will be recognized by those skilled in the arts of steroid chemistry and pharmaceutical preparations that many derivatives can be made which are biologically and chemically equivalent to, or even more active than, the indicated compound. Examples of equivalent compounds include esters of acid functions or esters or ethers of hydroxylic functions, or common carbonyl derivatives of carbonyl functions.

"Substantially pure", when used to describe the state of the Natriuretic Hormone, denotes the hormone essentially free of proteins, steroids, and other materials normally associated or occurring with Natriuretic Hormone in its native environment.

As used herein, the term "post salt peak" refers to material eluted from a G-25 Sephadex column which appears immediately after the sodium, potassium, urea and creatinine containing fractions and which has baseline conductivity and UV absorbance at 280 nm.

The biological activity of the Natriuretic Hormone can be determined by a number of assay techniques which involve sodium transport in a wide variety of cell types and in a number of animal species. For example, transepithelial sodium transport is inhibited in the isolated urinary bladder of the toad, in the isolated skin of the frog and in the isolated perfused cortical collecting tubule of the rabbit nephron. In all three structures, inhibition of sodium transport occurs only if the Natriuretic Hormone is added to the blood side of the structure. In the isolated tubule preparation, the addition of surface produces a decrease in sodium efflux (lumen to bath), but there is no effect if it is added to the lumen surface. There is a simultaneous decrease in the transepithelial electrical potential difference (P.D.) with the lumen becoming less positive. In dose response studies, both sodium efflux and P.D. approach zero. As used herein, the term "biologically active" refers to material which results in greater than 20% inhibition of $^{86}Rb$ uptake as measured by the method of Example II.

In addition, the Natriuretic Hormone produces an increase in sodium excretion in the normal Sprague-Dawley rat when fasted but allowed free access to water. It also produces natriuresis in an unanesthetized uremic rat. When the hormone is infused directly into the renal artery of the normal rat kidney, natriuresis is moderate. When the equivalent dose is infused into the renal artery of the kidney of a uremic animal, the natriuretic response is markedly increased.

The Natriuretic Hormone inhibits sodium transport by MDBK cells, a cell line originally obtained from bovine renal tubules and maintained using cell culture techniques. Such a cell line is available from the American Type Culture Collection, 12301 Park Lawn Drive, Rockville, Md. 20852. USA, where it is identified by the reference ATCC CCL34 (certified cell line). The preferred method of assaying bioactivity according to the present invention, described in Example II below, employs a microassay which is based upon the ability of the natriuretic compound of the present invention to inhibit $^{86}Rb$ influx by MDBK cells grown in culture. Ouabain ($10^{-5}M$) is used as the reference inhibitor. Natriuretic Hormone also inhibits sodium efflux and influx (in short-term measurements) as well as $^{86}Rb$ by the MDBK cell line in culture.

The Natriuretic Hormone of the invention can be used in a number of clinical and diagnostic contexts. Clinical indications include edematous conditions, such as congestive heart failure, cirrhosis of the liver accompanied by edema or ascites, nephrotic syndrome, and hypertensive conditions. Because the compound of the invention is resistant to inactivation under acidic or alkaline conditions, oral ingestion is possible and preferred. However, administration by other routes, such as intravenous, intramuscular, transdermal and the like, is also effective.

The amount administered at any one time will increase sodium excretion sufficiently to provide a beneficial clinical result. Later doses can be adjusted in accordance with clinical effects of the initial dose. A typical initial dose would be from about 1–1000 mg in an average human, preferably 10–250 mg, and more preferably 25–100 mg. The total daily dose can consist of a single individual dose or multiple doses given at intervals.

Pharmaceutical preparations can include, in addition to the active compound, various inert carriers and/or other inactive components such as moistening agents, flavors, binding agents, and extenders, as well as other compounds having pharmacological activities, such as other diuretics which increase the distal delivery of sodium (i.e., acetazolamide).

The pharmaceutical compositions can take the form of tablets, capsules, injectable solutions and suspensions, oral solutions, and other formulations intended for pharmaceutical use. For example, a composition intended for use in a tablet could contain 25 mg active material, calcium stearate, calcium sulfate, microcrystalline cellulose, peppermint oil, polysorbate 80, povidone, and pregelatinized starch.

In addition to use in humans, the natriuretic compound of the invention can be used for similar veterinary purposes in domesticated animals, particularly pets with sodium retaining diseases and high blood pressure.

The following examples are intended to illustrate but not limit the invention. While they are typical of those that might be used, other procedures known to those skilled in the art may be alternatively employed.

EXAMPLE I

Isolation of Natriuretic Hormone

Twenty four hour urine samples were collected over periods of one to ten days from non-dialyzed patients with serum creatinine concentrations of over 8 mg/dl and/or a serum creatinine clearance of less than 20–25 ml/minute. Notation was made of the volume of urine collected each day, and of all medications taken by the patient. Each 24 hour urine collection was lyophilized to a sludge under reduced pressure and temperature and reconstituted in 100 ml of deionized water. The preparation was then centrifuged at 3000 rpm at 4° C. and filtered through fluted filter papers, (Whatmann #1).

In brief, 25 ml aliquots of the concentrated urine samples, equivalent to 6 hour samples of original urine, were applied to individual 2.5×95-cm columns packed with Sephadex G-25 (fine grade, Phamacia Fine Chemicals, Inc., Piscataway, N.J.). Elution was carried out at 4° C. by gravity at a rate of 55 to 65 ml/h with a solution of 10 mM ammonium acetate at pH 6.8. The effluent solution was collected overnight in 18×150-mm glass tubes (12 ml) using an automated fraction collector (model 7000 Ultrorac, LKB Producer AB, Stockholm, Sweden). On the basis of the ultraviolet absorption at 280 nm (LKB Uvicord) and of the electrical conductivity tracings (model 5300B Conductolyzer with 5312B Conductivity cell, LKB Producter AB), the effluent solution and the contents of the tubes were pooled into several different fractions. The fractions containing high molecular weight compounds (e.g., proteins), sodium, potassium, urea, and creatinine were discarded. Natriuretic activity was present only in the fractions appearing immediately after the salt peak. Only this portion of the effluent solution was then routinely prepared by pooling the contents of 10 consecutive tubes (120 ml total) starting with the tube in which the specific conductance of the eluate had returned to base-line values and lyophilizing the material to dryness overnight in a glass container.

The dried eluate was then dissolved in 3.0 ml of distilled water, transferred into a screw cap glass or polyethylene vial, and stored at −80° C. Each milliliter of this solution was equivalent to the volume of original urine excreted in approximately 2 h. Storage of the concentrated urine samples or of the final fractions for periods of up to several months was found to have no influence on the natriuretic activity of the material.

The standard fractions subjected to assay, whether obtained from uremic patients or normal subjects, typically contained less than 10 meq/liter of sodium and 1 meq/liter of potassium. Differences were not observed between fractions from uremic patients and normal subjects for ammonium, urea, and protein concentrations. The mean values were: ammonium, 24.4±3.7 meq/liter; urea, 15.8±2.6 mg/100 ml; and protein, 2.0±0.6 mg/ml.

Biologically active fractions, as determined by the method of Example II, of post salt peak from the G-25 eluate were applied to a reverse phase chromatography column RP-C-18 (Altex Scientific, Berkeley, Calif., now Beckman Instruments, Brea, Calif.) and eluted with a continuous gradient of 0.2M pyridinium acetate (PH 5.5)/methanol (20–60% methanol). Individual tubes were evaporated to dryness employing a "Speed Vacuum" (Savant Instruments, Farmingday, N.Y), redissolved in deionized water, then tested for biological activity by the method of Example II. Employing the same column, the combined active fractions were recombined, re-chromatographed two additional times and eluted with 45% methanol/0.2M pyridinium acetate (PH 5.5). After each HPLC run, the resulting active fractions were combined and taken to dryness as above. The fractions were redissolved in deionized water and reassayed for biological activity.

The ultraviolet absorption spectrum of this material exhibited maxima at approximately 220 and 290 nm. The material exhibited intrinsic fluorescence in a Beckman Fluorometer, Beckman Instruments, Brea, Calif.

The biologically active material was then reacted with a large excess of 1:1 pyridine:BSTFA (bistrimethylsilyl trifluoroacetamide) at 50° for 30 minutes. The resulting mixture was then applied to a gas chromatograph, using a 15 meter fused silica capillary column (J&W Scientific DB-5-30W) employing a high resolution E-I mass spectrometer as a detector. The retention time of the single product was 200 to 700 seconds. No other products were detected. The trimethylsilyl groups were hydrolyzed by treatment with 1N hydrochloric acid for one hour giving, after lyophilization, a substantially pure white solid, the Natriuretic Hormone.

EXAMPLE II

Microassay For Biological Activity

The natriuretic activity of the Natriuretic Hormone can be ascertained by its effect on the uptake of $^{86}Rb$ by MDBK (Malbin Darby Bovine Kidney Cell) cultures. Briefly, uptake by the cells of $^{86}Rb$ (which behaves biologically as potassium) is inhibited by factors which inhibit the activity of the enzyme, Na-K-ATPase. Ouabain is a known inhibitor of this enzyme and the addition of ouabain to an MDBK cell preparation containing $^{86}Rb$ can result in as much as 90% inhibition of $^{86}Rb$ intake by the cells.

Approximately 200,000 MDBK cells were plated in trays containing 12 2 $mm^2$ wells, and grown for four days at 37° C. in Dulbecco's modified Eagle media (DMEM) (Gibco #430–2100), to which was added (per liter) 3.7 g sodium bicarbonate, 5 mg phenol red, 10% fetal calf serum, $10^6$ units penicillin-G sulfate, 0.1 g equivalent base streptomycin sulfate, 7.34 mg polymyxin-B sulfate, and 3.4 mg fungizone and maintained in an atmosphere of 5% $CO_2$, 95% air. The cells became confluent and present at a concentration of approximately $10^6$ cells per well. To perform the assay, the cells were preincubated for thirty minutes with the test material 50–75 ul in volume which represents at least 2–5 minutes of original urine, in fortified DMEM (500 $\mu l$) at 37° C. After this preincubation, approximately $5 \times 10^5$ cpm $^{86}Rb$ and an additional 50–75 $\mu l$ of test material were added to each well and the cells incubated at 37° C. for an additional 15 minutes. The reaction was stopped with 1 ml of cold PBS and washed twice with 0.5 ml of cold PBS. The washes were discarded. 0.5 ml of 5% TCA was added to each well and incubated for 10 minutes at 37° C. to release radioactivity inside the cells. The supernatents from each well were then transferred to a microfuge tube (1 ml). A 100 $\mu l$ aliquot (in duplicate) was transferred to scintillation vials containing scintillation fluid (Ready Safe for aqueous samples; Beckman Instruments, Brea, Calif.). The $^{86}Rb$ activity was counted in a scintillation counter (Beckman LS 3-801). The cells were then washed with PBS and digested overnight at 37° C. in 500 μL 0.1N NaOH. The next day, the hydrolyzed cells were analyzed for protein by the micro Coomassie method (Chiapelli, F. et al., *Analytical Bioch.*, 94:160 1974), which is incorporated herein by reference. In each set of assays, PBS and $10^{-5}$M Ouabain were used for negative and positive controls, respectively. Data were recorded as cpm/mg cell protein. Fractions which inhibited $^{86}$Rb uptake by more than 20% were considered active. Most active samples inhibited $^{86}$Rb uptake by a substantially greater percentage. Typical results are shown in Table I.

Although the invention has been described with reference to the presently preferred embodiment, it should be understood that various modifications can be made without departing from the spirit of the invention. Accordingly, the invention is limited only by the following claims.

TABLE I

| Each sample run in duplicate and averaged. | | |
|---|---|---|
| | cpm/mg of protein | % inhibition |
| Control + PBS | 79,692 | 0% |
| | 69,058 | |
| Ouabain$^{10-5}$ | 17,649 | 77.7% |
| | 15,611 | |
| G-25 "Post Salt" Natriuetic Activity | | |
| (10 uL) | 45,592 | 41.4% |
| | 41,596 | |
| (50 uL) | 32,336 | 58.0% |
| | 20,803 | |

We claim:

1. A substantially purified natriuretic hormone comprising a compound characterized by its ability to increase sodium excretion in the urine in mammals without a corresponding increase in potassium excretion wherein said compound:
   (i) has a molecular weight of about 360;
   (ii) has a molecular formula of $C_{21}H_{28}O_5$;
   (iii) has a steroidal nucleus;
   (iv) is a white powder;
   (v) exhibits a major ultraviolet absorbance peak at about 220 nm and a broad secondary peak at about 290 nm;
   (vi) is highly resistant to temperature extremes, maintaining biological activity after over a year of exposure to $-80°$ C. or vigorous boiling;
   (vii) is water soluble;
   (viii) is soluble in organic solvents with high dielectric constants;
   (ix) exhibits a markedly lower biological activity when exposed to 5N HCl;
   (x) inhibits transepithelial sodium transport
      (1) in the isolated urinary bladder of the toad;
      (2) in the isolated skin of the frog;
      (3) in the isolated perfused cortical collecting tubule of the rabbit nephron;
   (xi) produces an increase in sodium excretion in the normal Sprague-Dawley rat when fasted but allowed free access to water;
   (xii) produces natriuresis in an unanesthetized uremic rat; and
   (xiii) inhibits sodium transport by MDBK cells.

2. A pharmaceutical composition useful for treating mammals with edematous conditions or hypertension comprising an amount of the compound of claim 1 effective to treat said edematous conditions or hypertension and a pharmaceutical acceptable carrier.

3. A method of treating edematous conditions or hypertension in a mammal suffering therefrom by administering a therapeutically effective amount of the compound of claim 1 to said mammal.

4. A pharmaceutical composition of claim 2 wherein said compound is present in an amount of about 1-1000 mg.

5. A pharmaceutical composition of claim 2 wherein said compound is present in an amount of about 10-250 mg.

6. A pharmaceutical composition of claim 2 wherein said compound is present in an amount of about 25-100 mg.

7. A pharmaceutical composition of claim 2 wherein said carrier comprises moistening agents, flavors, binding agents and extenders.

8. A pharmaceutical composition of claim 2 wherein said composition is in a form selected from a group consisting of tablets, capsules, injectable solutions, suspensions and oral solutions.

9. A pharmaceutical composition of claim 2 wherein said tablets comprises about 25 mg of said compound, calcium stearate, calcium sulfate, microcrystalline cellulose, peppermint oil, polysorbate 80, povidone and pregelatinized starch.

10. A method of treating edematous conditions or hypertension in a mammal suffering therefrom by administering a therapeutically effective amount of the compound of claim 8 to said mammal.

11. A pharmaceutical composition of claim 9 wherein said compound is present in an amount of about 1-1000 mg.

12. A pharmaceutical composition of claim 9 wherein said compound is present in an amount of about 10-250 mg.

13. A pharmaceutical composition of claim 9 wherein said compound is present in an amount of about 25-100 mg.

14. A pharmaceutical composition of claim 9 wherein said carrier comprises moistening agents, flavors, binding agents and extenders.

15. A pharmaceutical composition of claim 9 wherein said composition is in a form selected from a group consisting of tablets, capsules, injectable solutions, suspensions and oral solutions.

16. A pharmaceutical composition of claim 9 wherein said tablets comprises about 25 mg of said compound, calcium stearate, calcium sulfate, microcrystalline cellulose, peppermint oil, polysorbate 80, povidone and pregelatinized starch.

* * * * *